United States Patent
Ihrfelt et al.

(10) Patent No.: US 6,478,787 B1
(45) Date of Patent: Nov. 12, 2002

(54) DEVICE FOR THE SUPPORT OF AN ABSORBENT ARTICLE

(75) Inventors: Birgitta Ihrfelt, Västra Frölunda (SE); Terje Vigmo, Mölnlycke (SE); Peter Rönnberg, Mölndal (SE)

(73) Assignee: SCA Hygiene Products AB, Gothenburg (SE)

(*) Notice: Subject to any disclaimer, the term of this patent is extended or adjusted under 35 U.S.C. 154(b) by 0 days.

(21) Appl. No.: 09/499,292

(22) Filed: Feb. 7, 2000

Related U.S. Application Data

(63) Continuation-in-part of application No. 08/425,253, filed on Apr. 17, 1995, now abandoned, which is a continuation of application No. 08/069,680, filed on Jun. 1, 1993, now abandoned, which is a continuation of application No. 07/653,521, filed on Jan. 30, 1991, now abandoned, which is a continuation of application No. 07/399,495, filed on Sep. 6, 1989, now abandoned.

(30) Foreign Application Priority Data

Mar. 24, 1987 (SE) ................................ 8701208

(51) Int. Cl.[7] .......................... A61F 13/15; A61F 13/20
(52) U.S. Cl. ............................ 604/385.3; 604/385.03; 604/385.14; 604/391; 604/392; 604/400; 604/402
(58) Field of Search .................. 604/385.24–385.3, 604/385.14, 385.03, 386, 391, 392, 395, 400–402; 2/408, 919, 920, FOR 101

(56) References Cited

U.S. PATENT DOCUMENTS

| | | |
|---|---|---|
| 1,331,042 A | 1/1920 | Andreae |
| 2,175,786 A | 10/1939 | Smarr |
| 2,545,099 A | 3/1951 | Mann |
| 2,692,598 A | 10/1954 | Peet |
| 2,831,486 A | 4/1958 | Sanders |
| 2,863,456 A | 12/1958 | Leupold et al. |
| 2,871,859 A | 2/1959 | Dunn |
| 2,881,761 A | 4/1959 | Kenner |
| 3,057,354 A | 10/1962 | Roberts et al. |
| 3,094,990 A | 6/1963 | Neilson |
| 3,335,721 A | 8/1967 | Gastwirth |
| 3,359,980 A | 12/1967 | Rosenblatt |
| 3,441,025 A | 4/1969 | Ralph |
| 3,618,608 A | 11/1971 | Brink |
| 3,653,381 A | 4/1972 | Warnken |
| 3,993,074 A | 11/1976 | Murray et al. |
| 4,022,212 A | 5/1977 | Lovison |
| 4,031,897 A | 6/1977 | Graetz |
| 4,280,230 A * | 7/1981 | LaFleur ......................... 2/408 |
| 4,560,381 A | 12/1985 | Southwell |
| 4,579,556 A | 4/1986 | McFarland |
| 4,666,440 A | 5/1987 | Malfitano |
| 4,668,230 A | 5/1987 | Damico et al. |
| 4,802,469 A * | 2/1989 | Gollestani ...................... 2/408 |
| 4,904,249 A | 2/1990 | Miller |
| 4,964,860 A * | 10/1990 | Gipson et al. .............. 604/391 |
| H1440 H * | 5/1995 | New et al. .................. 604/402 |
| 5,549,593 A * | 8/1996 | Ygge et al. ................. 604/391 |
| 5,636,387 A * | 6/1997 | Lundy ............................ 2/408 |
| 5,651,779 A * | 7/1997 | Burrell ....................... 604/402 |
| 6,241,716 B1 * | 6/2001 | Ronnberg ................... 604/391 |

FOREIGN PATENT DOCUMENTS

| | | |
|---|---|---|
| CA | 1149104 | 7/1983 |
| DE | 1926289 | 8/1970 |
| DK | 71870 | 12/1950 |
| GB | 1200177 | 7/1970 |
| GB | 1263913 | 2/1972 |
| IT | 276660 | 4/1934 |
| JP | 38-22345 | 10/1963 |
| WO | WO86/02530 | 5/1986 |

* cited by examiner

Primary Examiner—Aaron J. Lewis
Assistant Examiner—K. M. Reichle
(74) Attorney, Agent, or Firm—Young & Thompson

(57) ABSTRACT

A combination of an absorbent article and a waist belt for supporting the article has coacting hook and loop fabric tape elements thereon by which the absorbent article and the waist belt are releasably secured to each other. The hook fabric tape elements are provided on one of the waist belt and the absorbent article, and the loop fabric tape elements are provided on the other of the waist belt and the absorbent article.

19 Claims, 15 Drawing Sheets

DEVICE FOR THE SUPPORT OF AN ABSORBENT ARTICLE

CROSS REFERENCES TO RELATED APPLICATIONS

This is a continuation-in-part of prior application Ser. No. 08/425,253 filed Apr. 17, 1995, which is a file wrapper continuation of Ser. No. 08/069,680 filed on Jun. 1, 1993, which is a file wrapper continuation of Ser. No. 07/653,521 filed Jan. 30, 1991, which is a file wrapper continuation of Ser. No. 07/399,495 filed Sept. 6, 1989, all now abandoned.

FIELD OF THE INVENTION

The present invention relates to a device for supporting an absorbent article such as an incontinence protector, a diaper or the like.

BACKGROUND OF THE INVENTION

Numerous types of devices are previously known. For example, elastic textile pants are often utilized to hold diapers or the like fixed in position during use. An alternative to such pants is the so-called all-in-one diaper which is composed of a plastic backing forming together with a diaper an integral unit. In its unused state, the most common type of all-in-one diapers is principally shaped as a pair of underpants with open side seams which are joined together with adhesive tape when using the diaper so as to make it seal like a pant around the user's abdomen.

By being both easily handled and readily replaceable, the all-in-one diapers are certainly most useful in practice. Among adults suffering from incontinence however, the wide range of individual variations as to degree of incontinence and to bodily shape and size makes it almost impossible for economic and manufacturing reasons to satisfy all demands with only a limited number of diaper variants available.

Therefore, a diaper fixed in position with the aid of a separate pant would be more useful for incontinent adults. By being able to chose the appropriate size of pant independent of the type of diaper required with regard to degree of incontinence, there is provided for the user a large selection of combination possibilities from only a restricted number of pant and diaper sizes.

There is however a drawback associated with complete diaper pants in that they are difficult to put on and replace on users of a specific category such as those incontinent, institutionalized patients who are heavy, immobile and incapable of standing on their legs, and bed-ridden or contractured patients. The use of complete pants, which have to be wrenched over the user's legs to be properly applied, naturally complicates diaper changes making it a time-consuming procedure for the nursing staff and awkward for the incontinent patient.

The application of pants which have to be threaded on over the feet may even cause trouble to disabled persons or those with coordination problems but otherwise capable of managing on their own at home.

SUMMARY OF THE INVENTION

The present invention aims to eliminate the problem associated with previously known items of this type.

This aim is accomplished by in combination, an absorbent article, such as an incontinence protector, a diaper or the like, having a transverse forward end, a transverse rear end, a longitudinal first side extremity, a longitudinal second side extremity, two forward corners and two rear corners joining the forward end and the rear end to the first side extremity and second side extremity, respectively, and a waist belt for supporting said absorbent article, said waist belt and said absorbent article having coacting hook and loop fabric tape elements thereon by which the diaper and the waist belt are releasably secured to each other. A forward and a rear portion of the diaper overlaps in the applied state of the article a forward and rear portion, respectively, of the waist belt, hook members or apertures being provided at least on the forward and rear ends of the article, the hook members and apertures being constituted by hook and loop fabric tape elements.

The combination including a waist strap or belt which is readily connectible with a diaper affords the possibility of selecting waist belt and diaper independently of one another. Moreover, application of the waist band, especially if openable, onto the user's body is a most simple procedure. An additional advantage is gained in that even those with restricted ability of turning or bending down may easily manage to change on their own a diaper attached to a waist belt according to the present invention. The manner of performing such a diaper change will be described in the following.

In contrast to complete pants, a waist belt according to the present invention will generally remain unsoiled when worn and may be used several times before it needs washing. Of course, waist belts intended to be discarded when soiled are also conceivable.

BRIEF DESCRIPTION OF THE DRAWINGS

A combination according to the invention will be described in more detail below with reference to the exemplary embodiments illustrated in the accompanying drawings, of which

DETAILED DESCRIPTION OF THE INVENTION

The diaper shown in FIGS. 1A–1H is of a conventional type, comprising a liquid permeable inner layer 2, a liquid impermeable outer layer 3, and enclosed there between an absorbent body 4.

Figure 3:
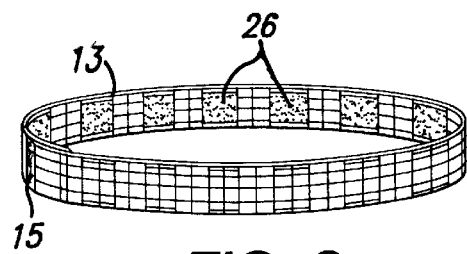

Bands 8, 9 provided with hooks or loops elements of tape type such as VELCRO are disposed at either transverse end 6, 7 of the diaper, which bands 8, 9 can be made of plastics or textile. The bands 8, 9 shown in FIGS. 1 and 3 are plastic bands provided with hooks or loops tape elements 10 extending along the whole length of the bands.

Bands 8 are provided at each side extremity of the forward transverse end 6 of the diaper. At the rear transverse end 7 bands 9 are provided. In the embodiment shown on FIG. 1A each band extends from a side extremity. The band has a greater extension in the transverse than in the longitudinal direction of the diaper. Only a part of each transverse end is covered with the hooks or loops tape elements-band. Preferably hook elements (male elements) are used on the bands on the diaper.

Figure 1A:
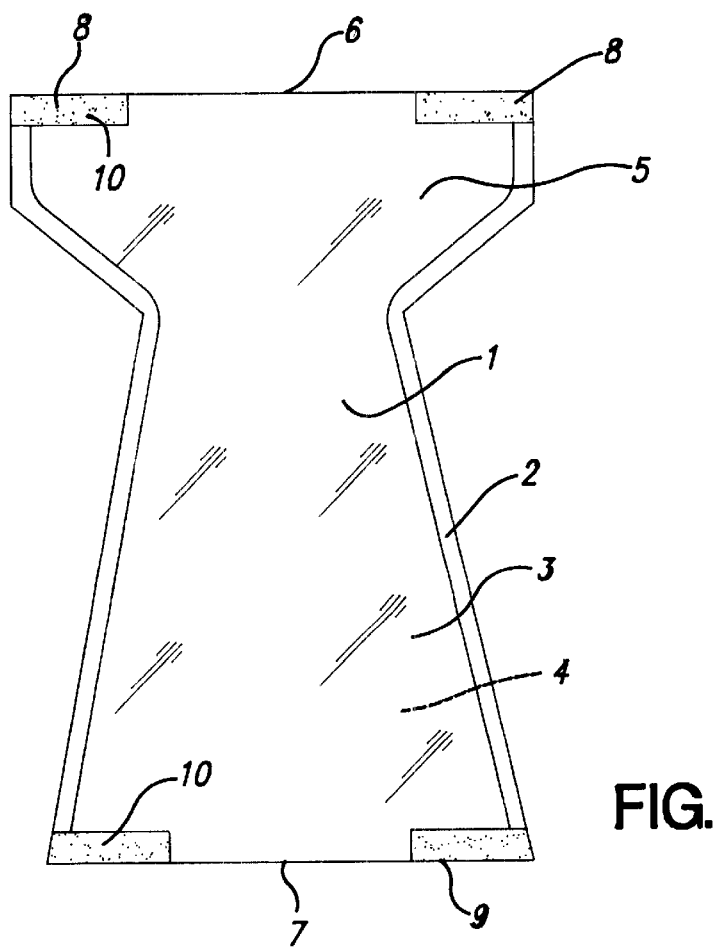
FIGS. 1A–1H show different embodiments of a diaper provided with the inventive attachment means.
Figure 1B:
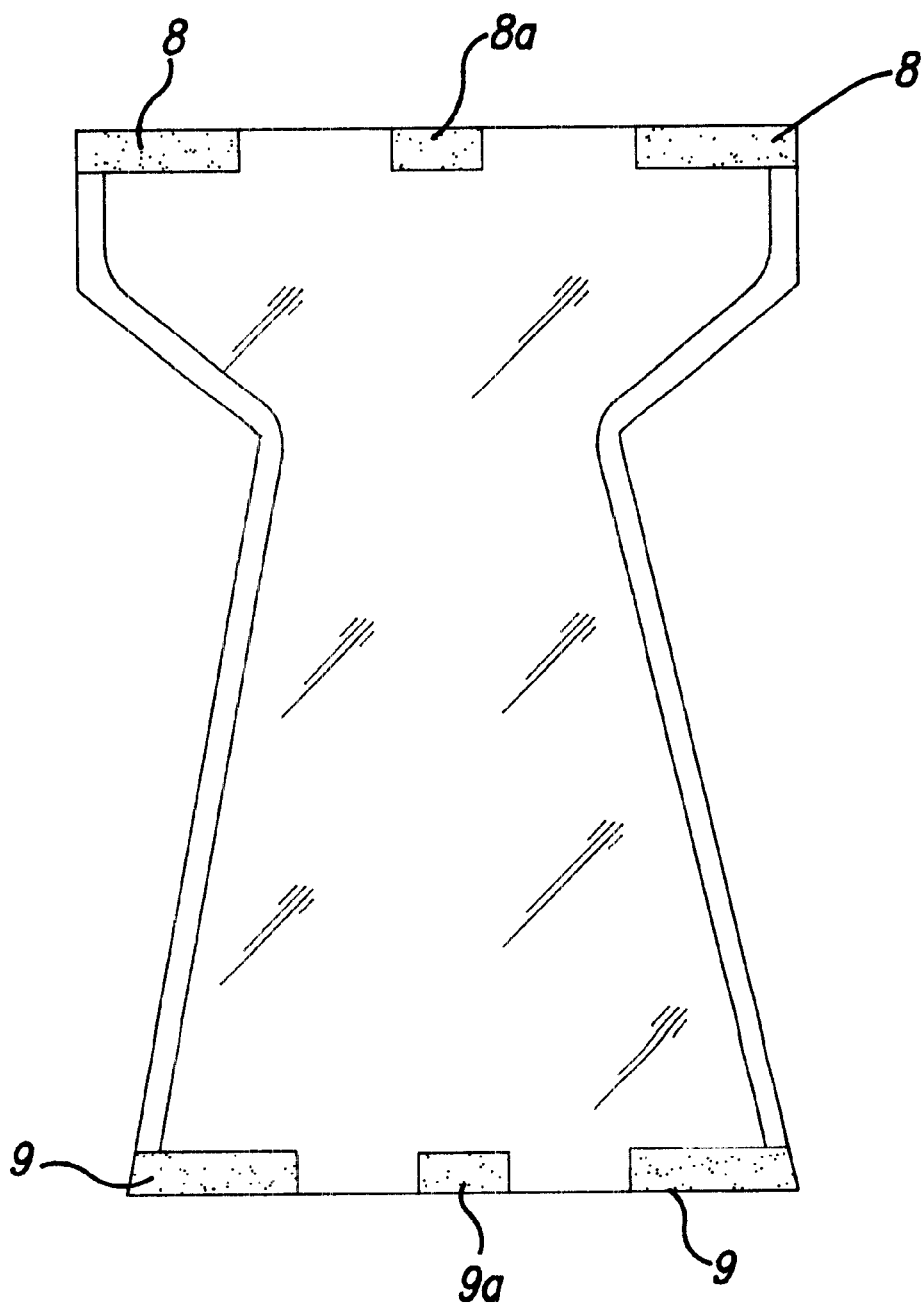
Figure 1C:
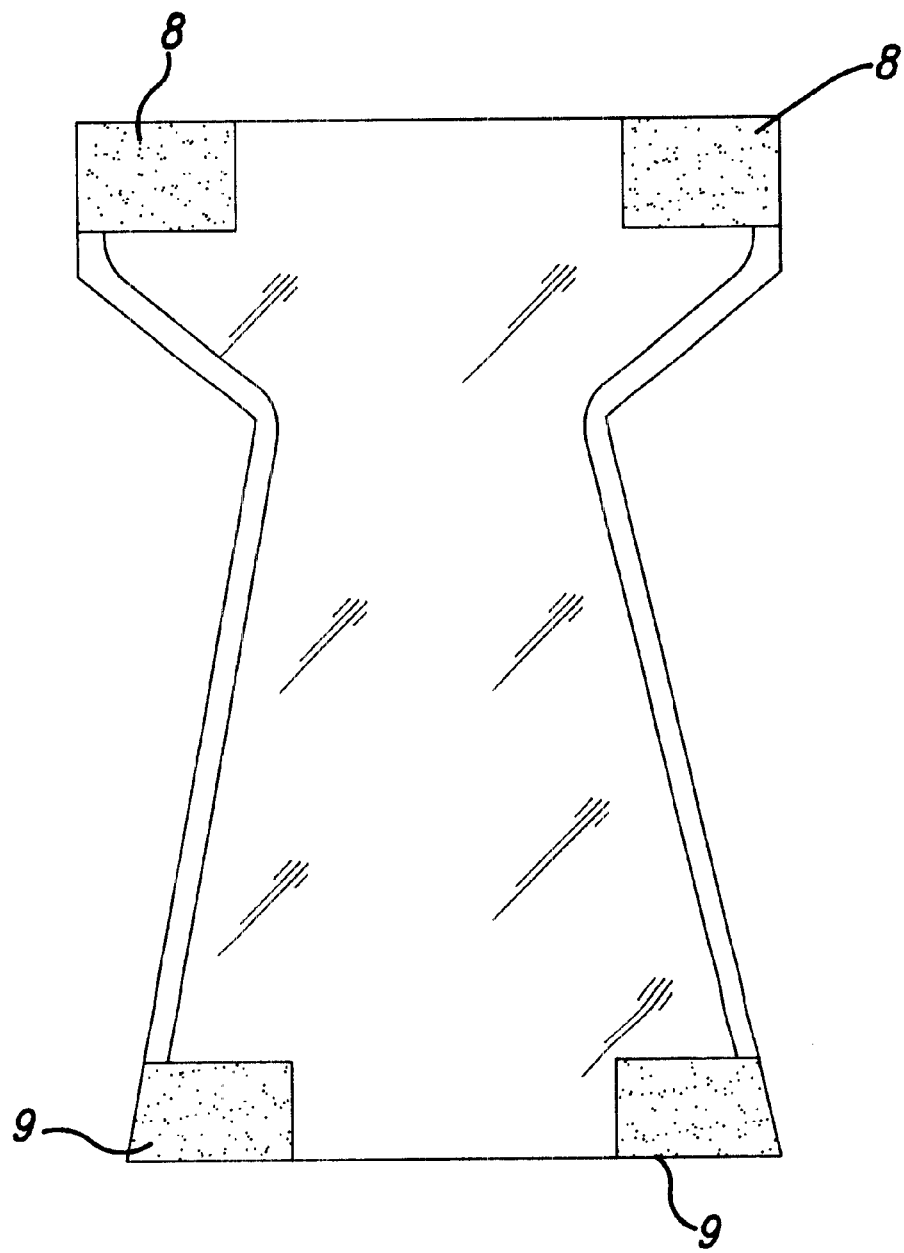

In FIG. 1B a further band element is used on each of the transverse ends of the diaper. In this case only one band element 8a, 9a is shown. However, it is possible to use several band elements spaced apart along each transverse end, as long as they are spaced apart enough to maintain the transverse ends relatively flexible and compliant to the user's belly and back side. In FIG. 1C band elements have a larger extension in the longitudinal direction of the diaper than the band elements shown in FIGS. 1A, 1B. In this way a better adjustability in the longitudinal direction of the diaper is obtained when fastening the diaper to the belt. In this case no extra fastening means in the middle of the transverse ends are shown. However, it is possible to use such further tape elements here also.

A further possible embodiment, which is not shown in any drawing, is to use only a band element 8a in the middle of the forward transverse end and tow or more band elements at the rear end of the diaper.

Figure 1D:
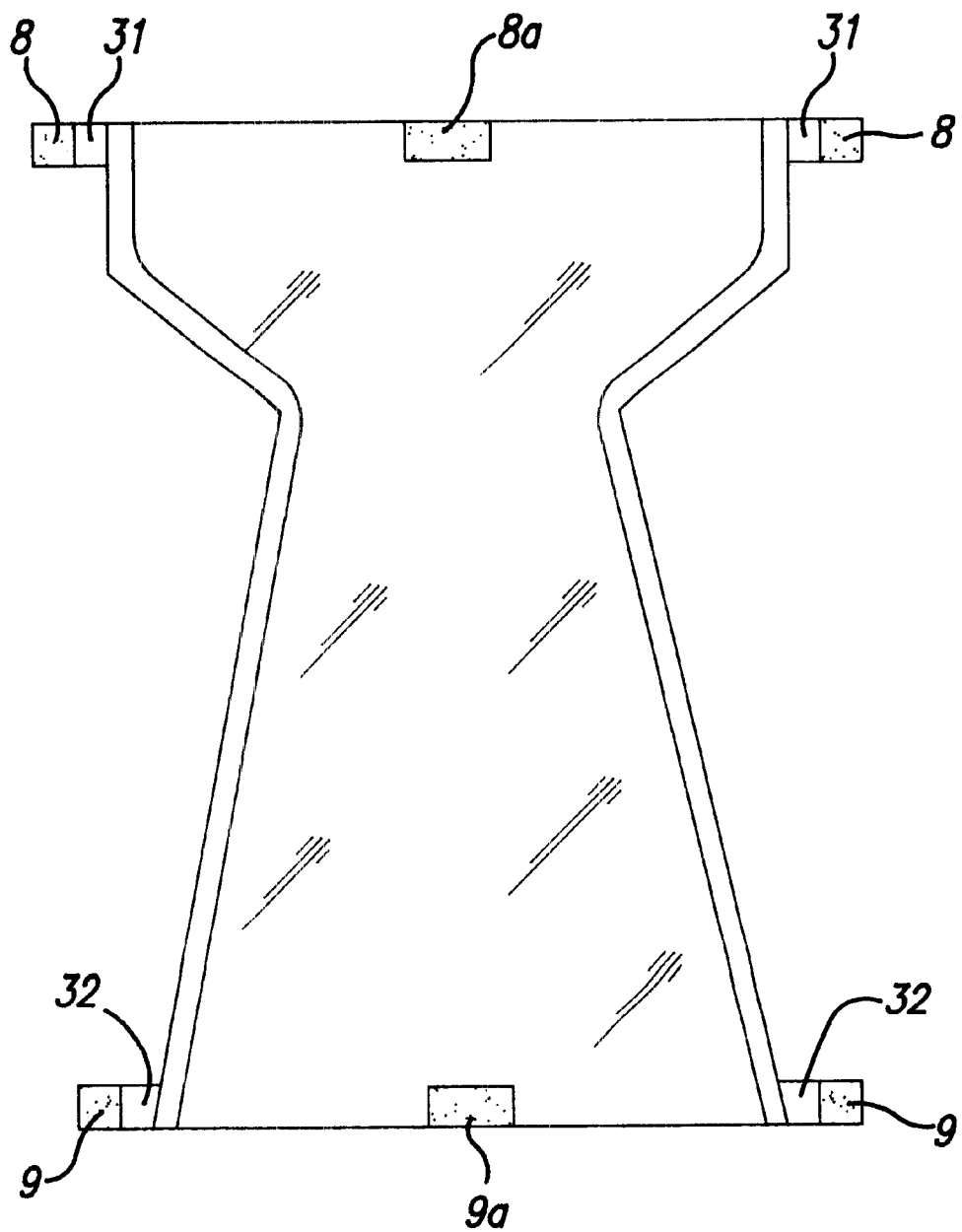
Figure 1E:
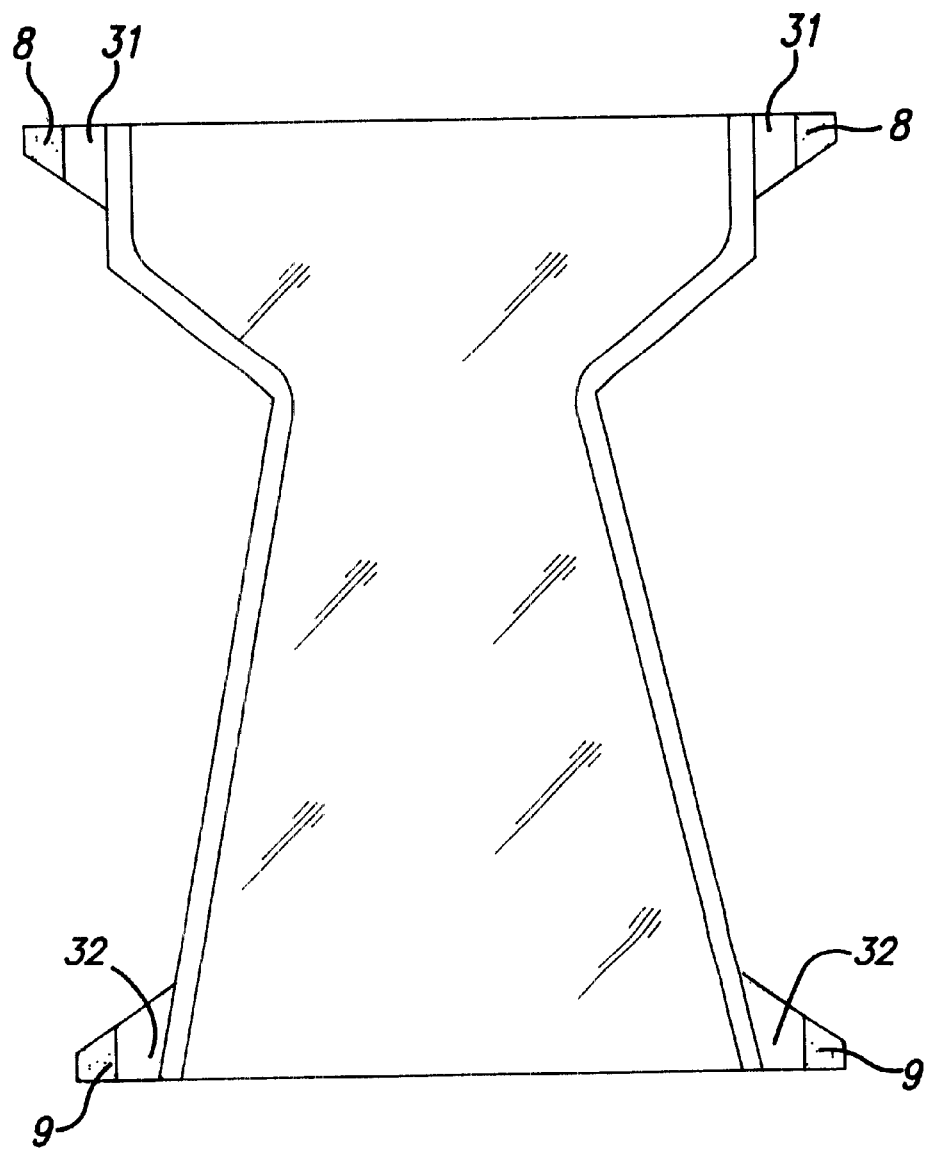

In FIG. 1D the diaper comprises end flaps as extensions of each transverse end of the diaper. On the forward side flaps 31 band elements 8 are arranged. On the rear side flaps 32 band elements 9 are arranged. The diaper also comprises extra fastening means consisting of a band element 8a at the middle of the forward transverse end and a band element 9a at the middle of the rear transverse end. In FIG. 1E an embodiment similar to that in FIG. 1D is shown. In FIG. 1E the side flaps are of a general triangular or trapezoidal form. In other respects this embodiment is the same as that in FIG. 1D, however, without the band elements 8a and 9a. It is of course possible to use such further band elements also in this embodiment.

Figure 1F:
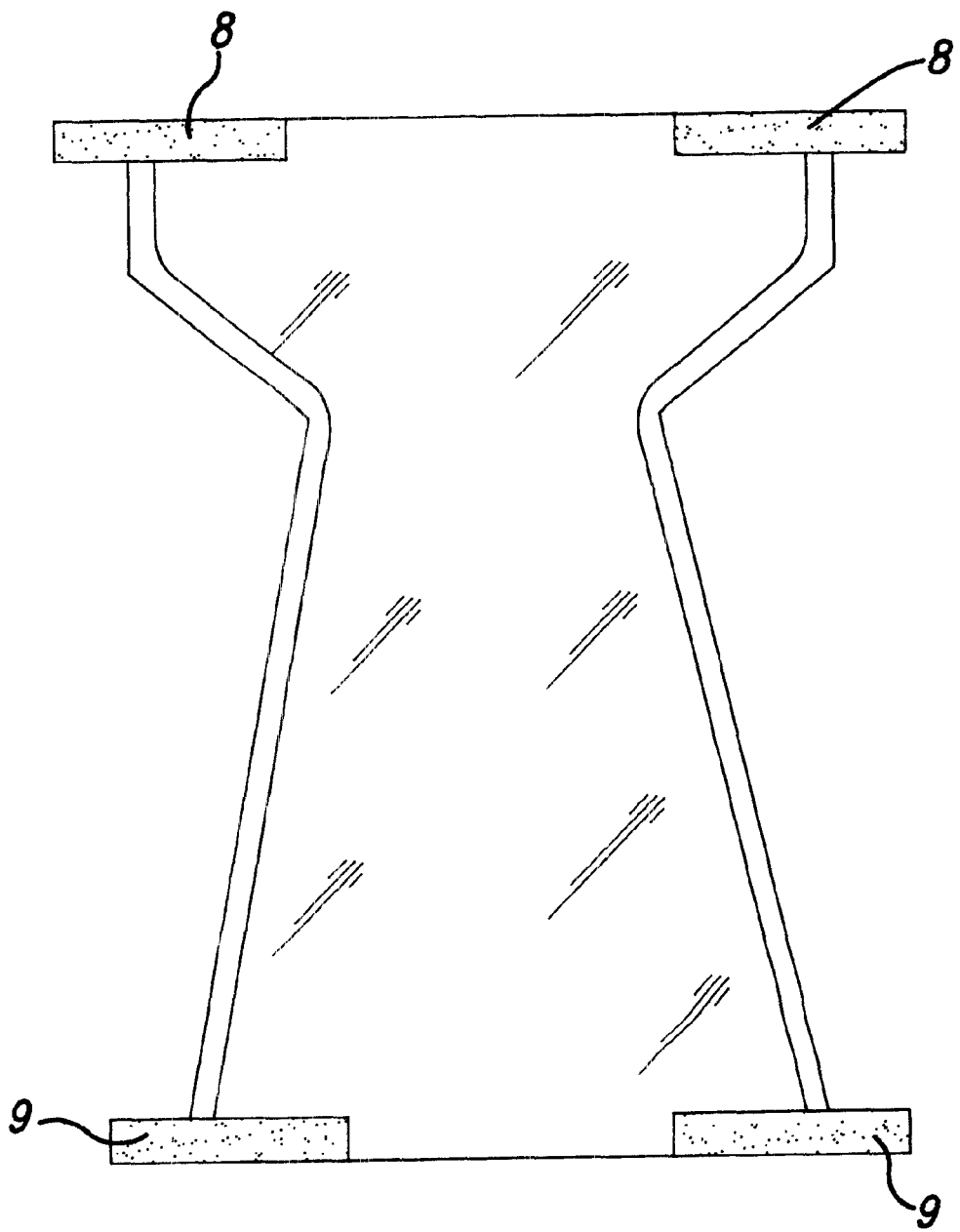

The embodiment shown in FIG. 1F comprises band elements 8 and 9 at the forward and rear transverse ends of the diaper. Each band element is extended, in the direction of the transverse end, outside the side extension as a side flap.

Figure 1G:
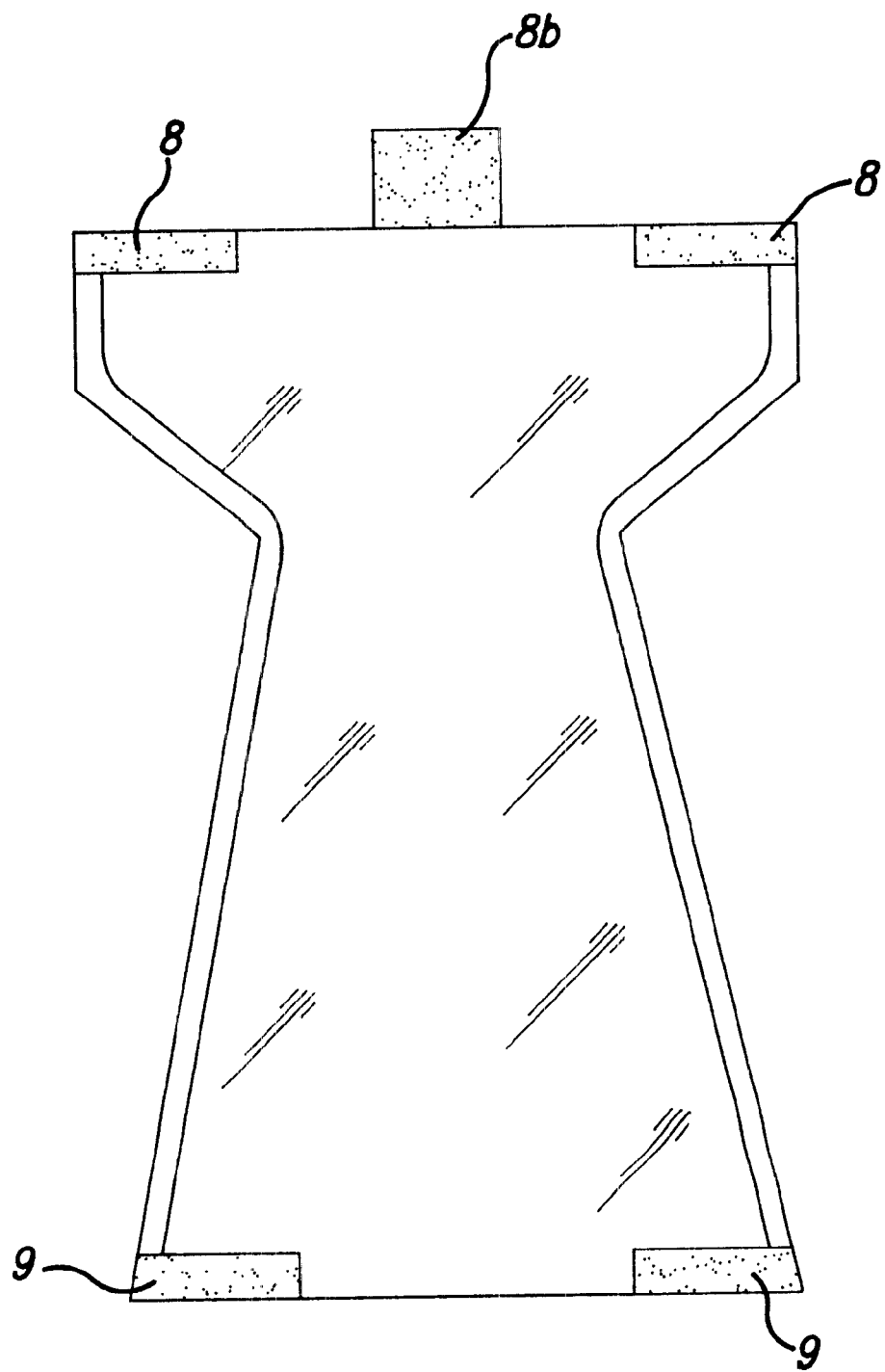
Figure 1H:
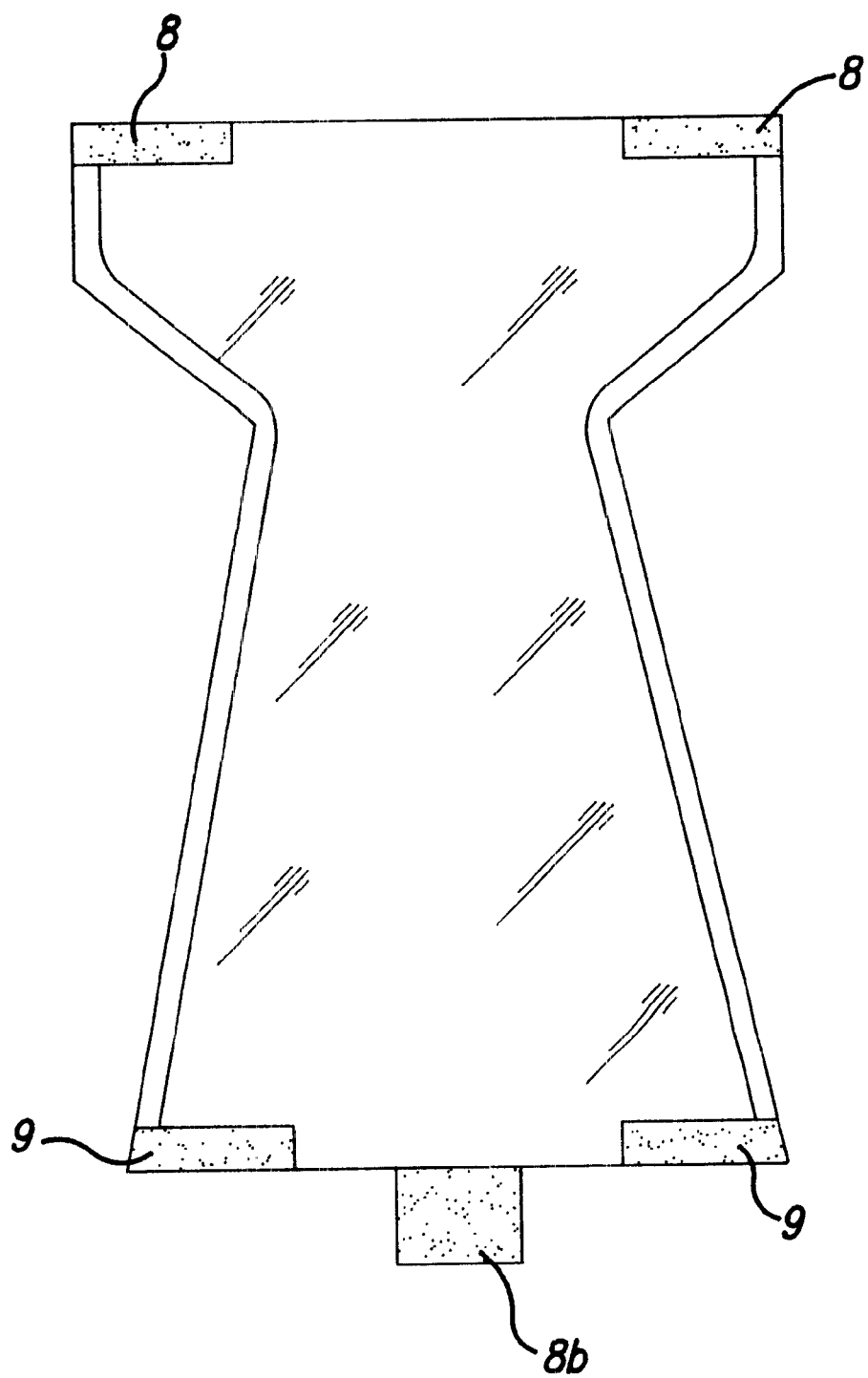
Figure 5A:
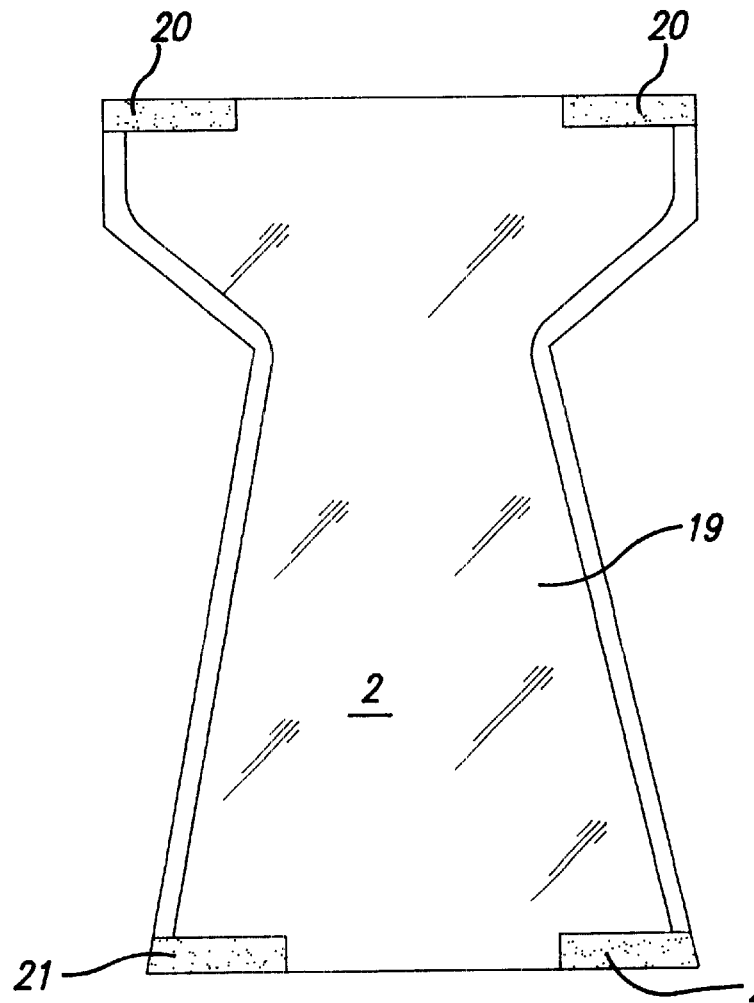
FIGS. 5A–5G show other embodiments of a diaper provided with the inventive attachment means.

FIG. 1G shows an embodiment similar to that of FIG. 1A, comprising an extra fastening element in the form of an end flap 8b extending from the middle part of the front end of the diaper, in the longitudinal direction thereof. Such an element may also be arranged at the rear transverse end as shown in FIG. 1H.

Figure 2:
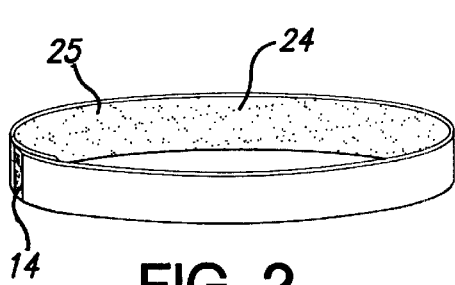
FIGS. 2, 3 and 4 show various embodiments of the inventive waist belt intended for use in combination with the diapers illustrated in FIGS. 1A–1H.

The diaper 1 shown in FIGS. 1A–1H is intended for use together with a waist belt having cooperating hooks or loops tape elements for engagement with the elements 10 provided on the bands 8, 9. Such waist belts are shown in FIGS. 2 and 3. The waist belt 24 of FIG. 2 is made of plastics or textile and comprises a hooks or loops tape element 25 along its inside whereas the waist belt 13 of FIG. 3 is made in the form of an elastic netting and comprises on its inside a row of hooks or loops tape elements 26 spaced from each other along the circumference of the belt. In order to facilitate application, the waist belts can be opened and closed with the aid of fastening means 14, 15 which in the exemplary embodiment also are hooks or loops type closures.

Figure 4:
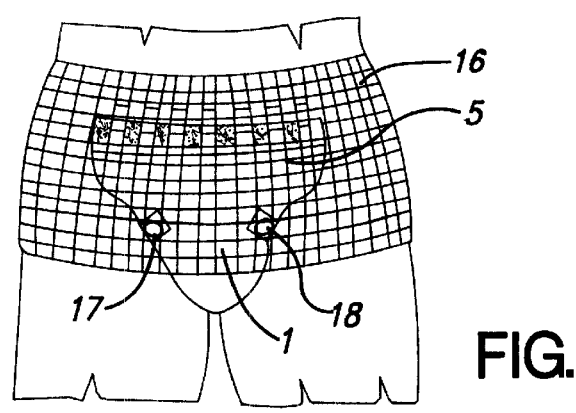

A waist belt 16 can be made wide enough, as in FIG. 4, to overlap the diaper 1 during use for holding it tightly pressed against the wearer's body. In this manner the diaper will remain more securely in position reducing thereby the risk of leakage past the diaper edges. With a wider waist belt 16, however, additional points of attachment 17, 18 may be required between the diaper and the waist belt. In the exemplary embodiment, such points of attachment 17, 18 are arranged at the groin region of the wearer.

Figure 6:
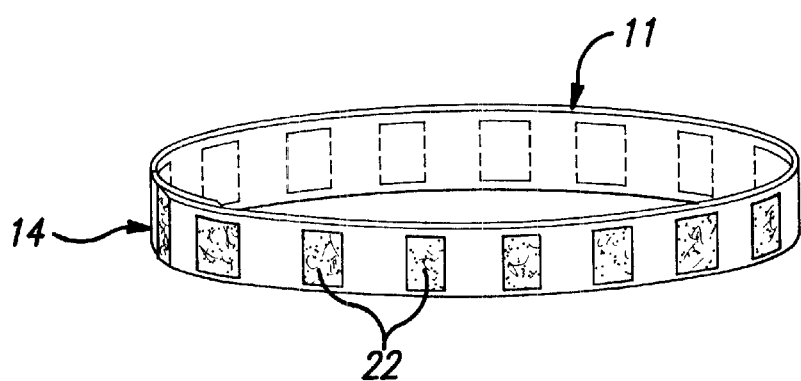
FIGS. 6 and 7 show different embodiments of waist belts intended for use in combination with the diaper illustrated in FIGS. 5A–5G.
Figure 5B:
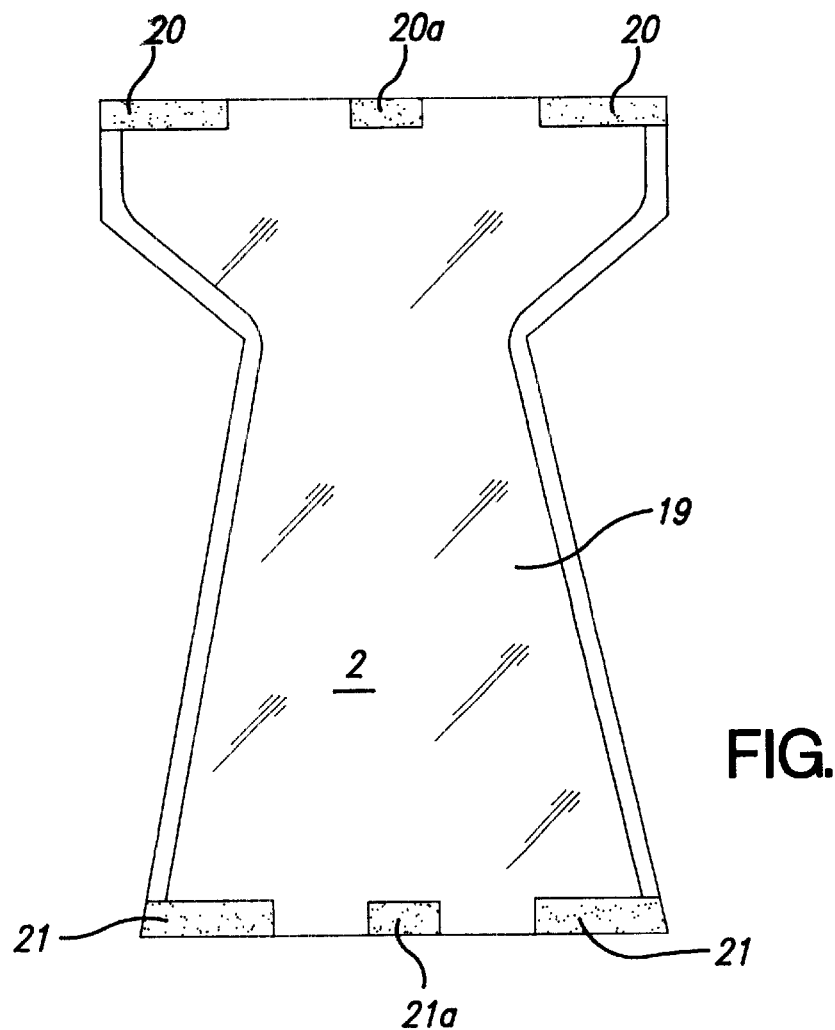
Figure 7:
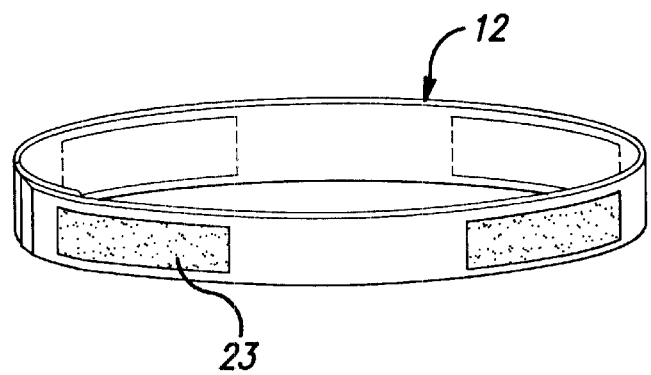
Figure 5C:
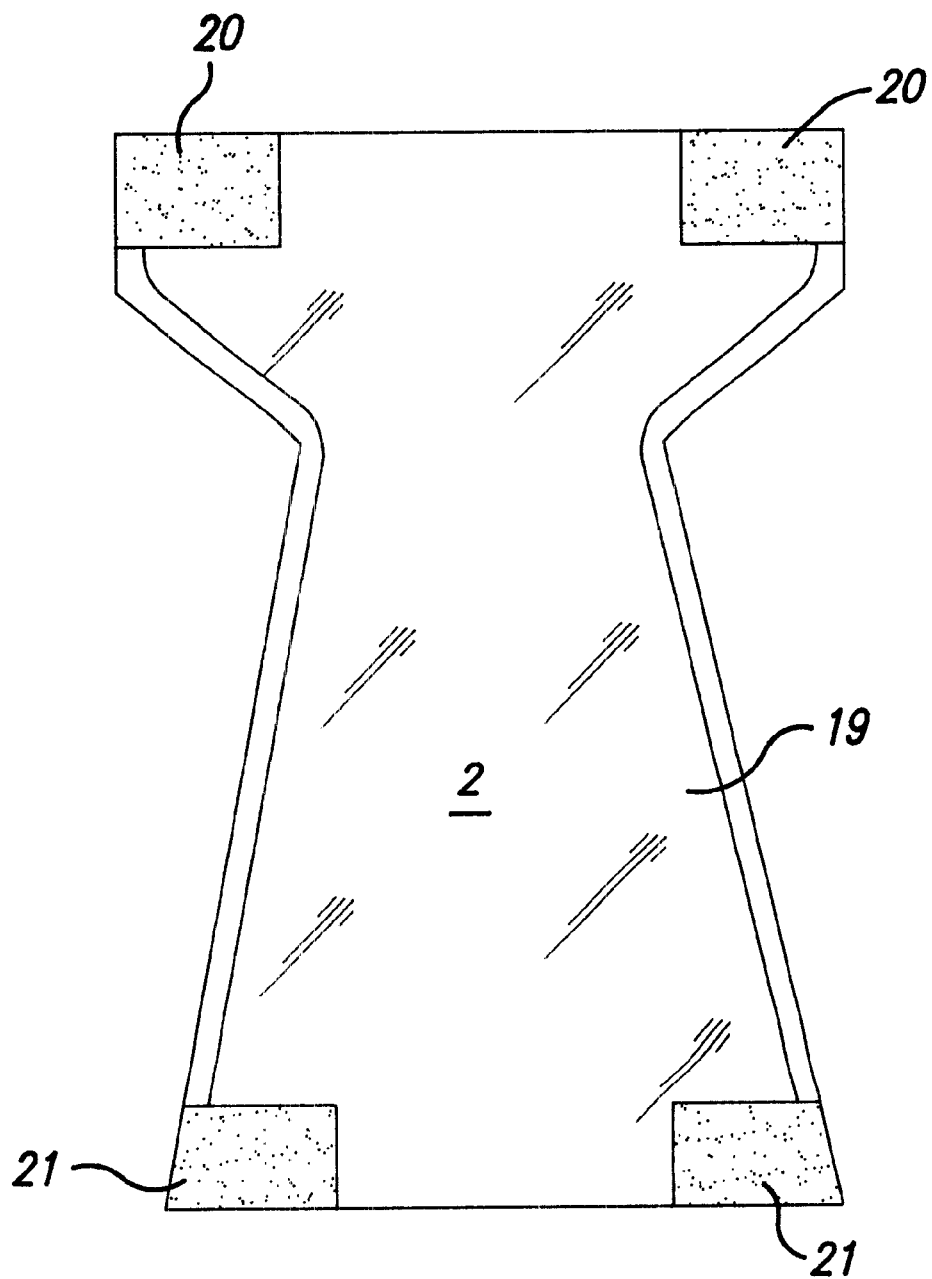
Figure 5D:
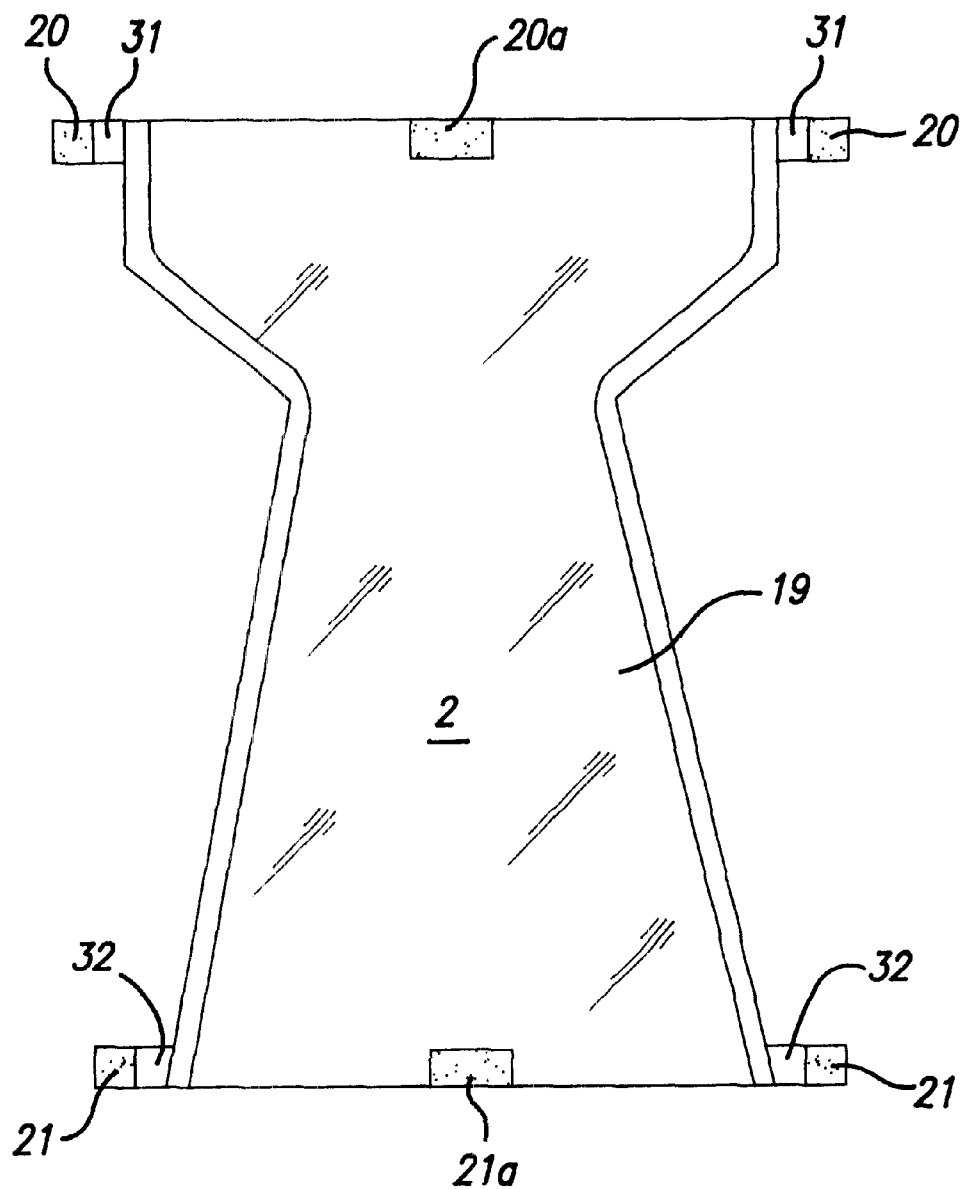
Figure 5E:
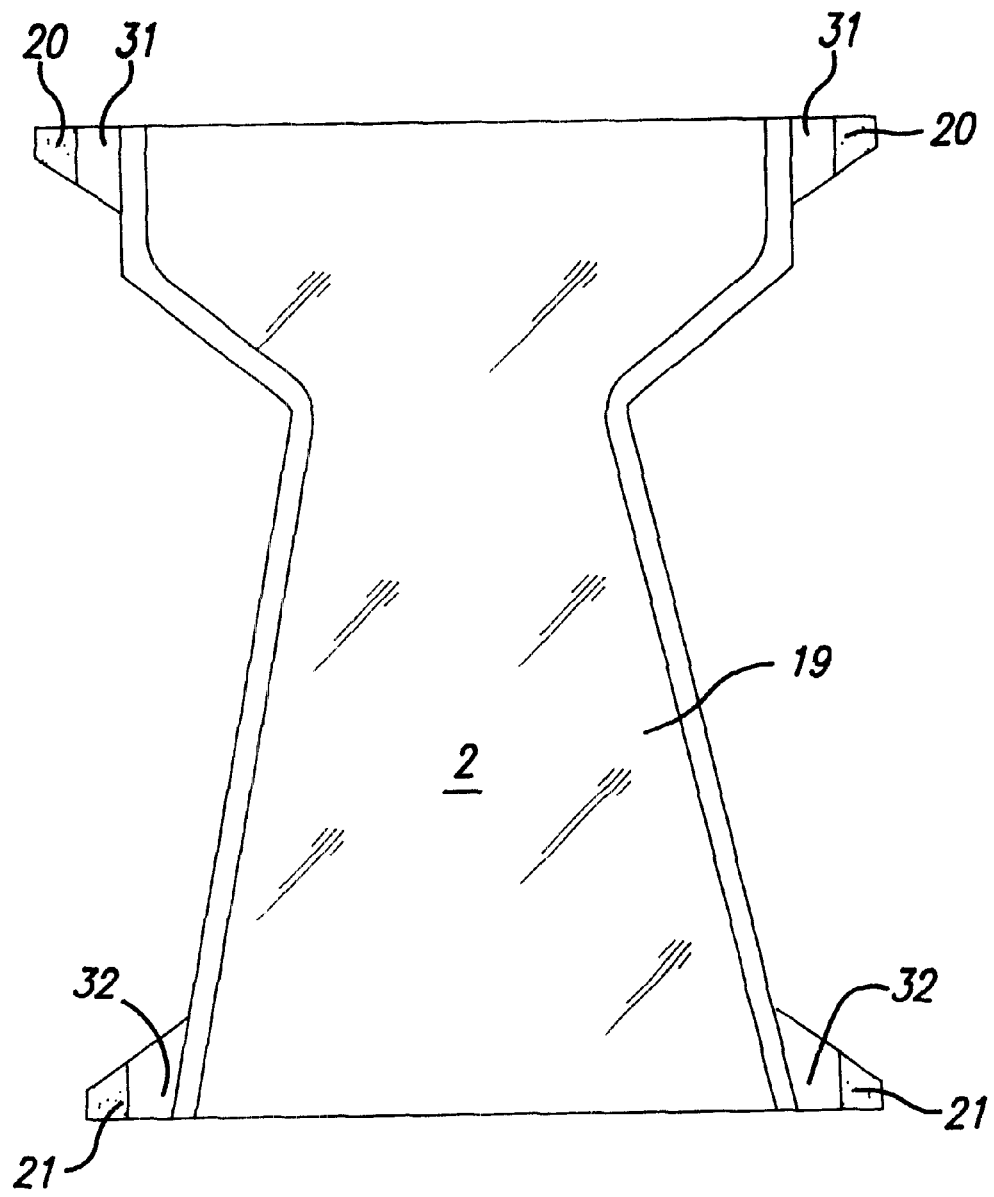
Figure 5F:
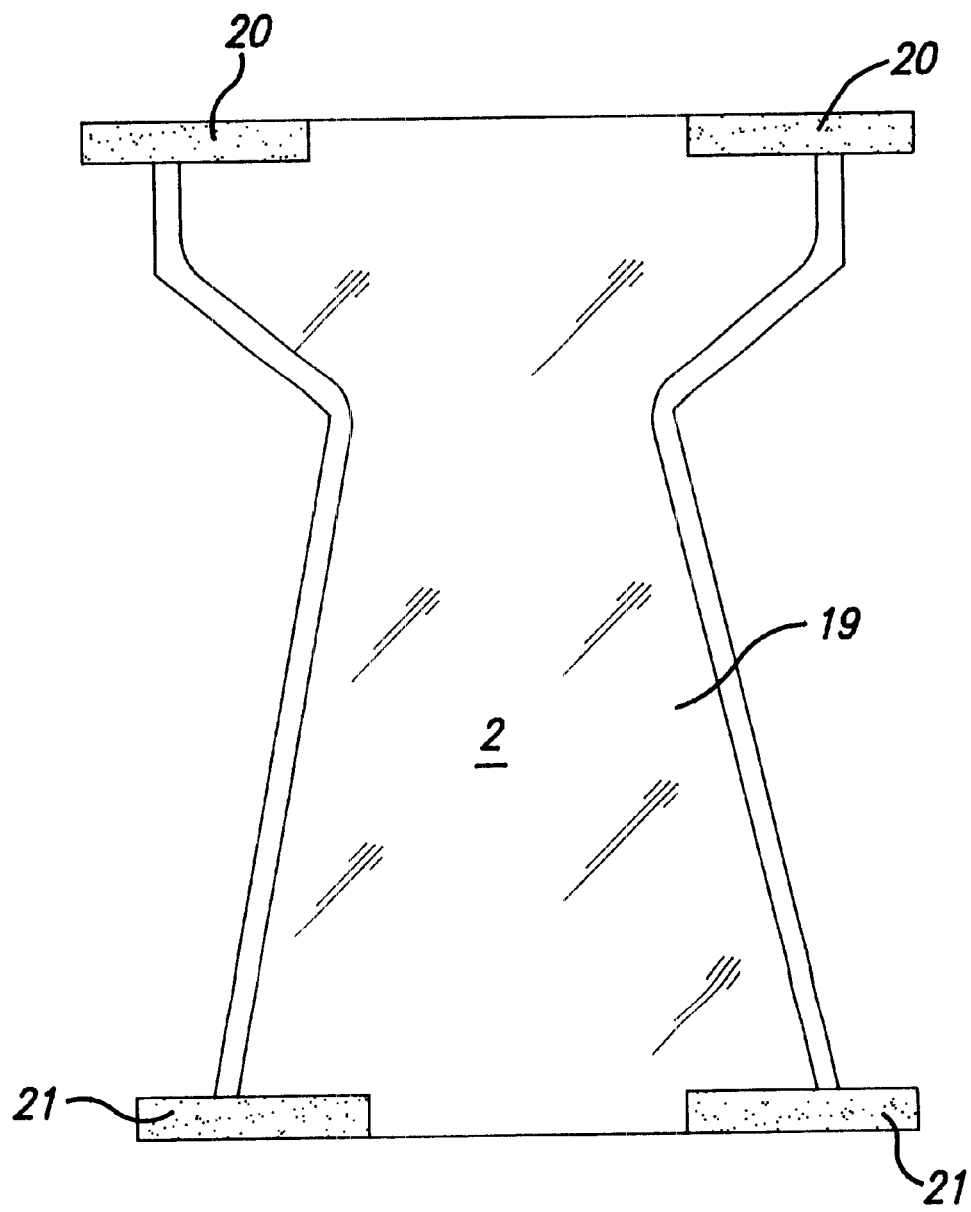
Figure 5G:
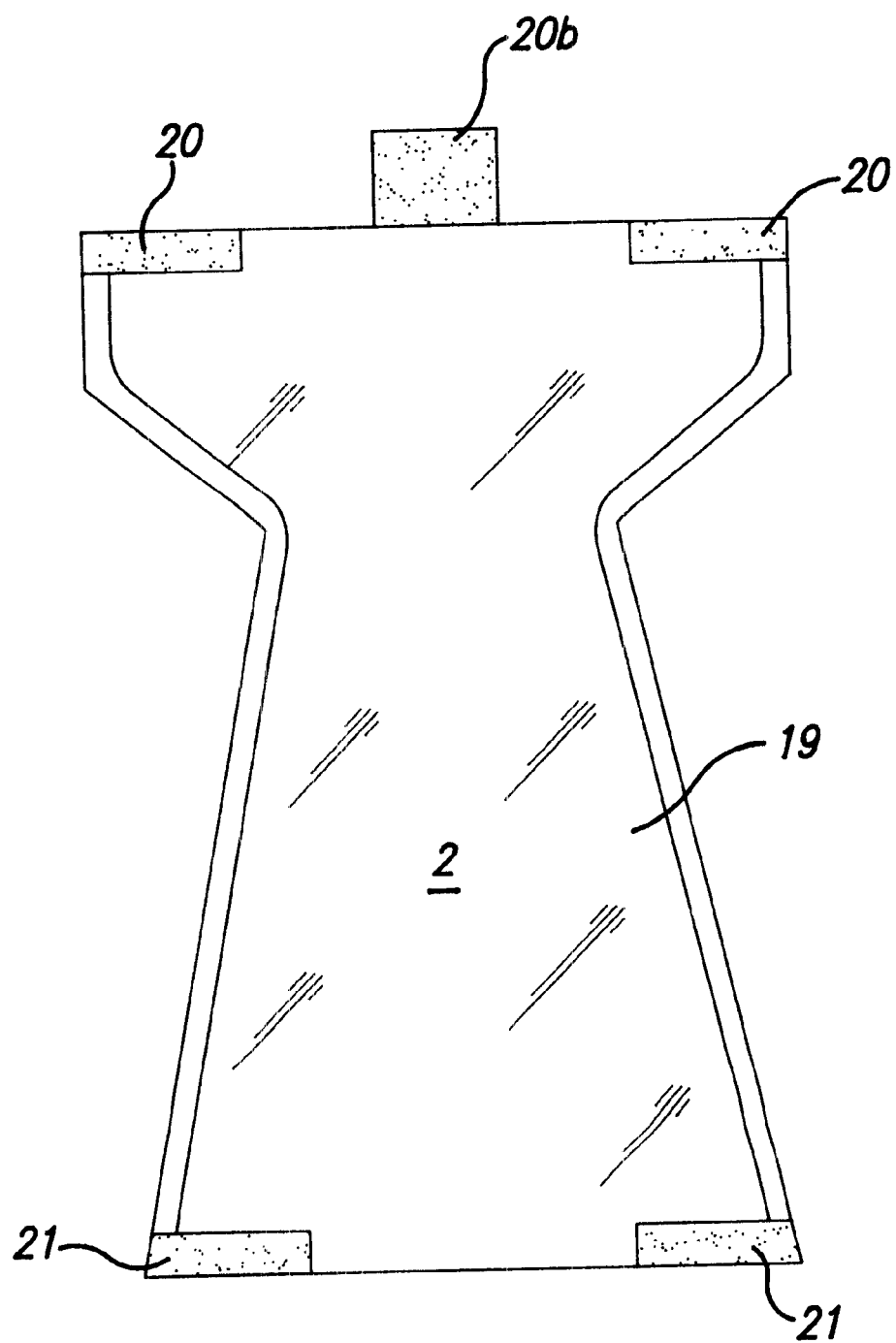

In FIGS. 5A–5G, a diaper 19 is shown which is identical to the diaper shown in FIGS. 1A–1G, except that the bands 20, 20a, 20b and 21, 21a, respectively, provided with hooks or loops tape elements are attached to the ends of diaper 19 on the side which in use faces the wearer, i.e. the side containing the liquid permeable inner layer 2. In such a case the cooperating tape elements on the waist belt must of course be placed on the outer side thereof. FIGS. 6 and 7 disclose such waist belts 11 and 12, respectively, having tape elements 22 and 23, respectively, of different lengths extending spaced from each other along the circumference of the waist belt. The tape elements 22 and 23 extend substantially over the whole width of the belt. For belts of inelastic material, a continuous tape element can be used but in order not to impair in a too great extent the elasticity of a belt of elastic material a row of mutually spaced tape elements is preferred for such belts.

Advantageously, the application of a diaper and the inventive waist belt onto a user's body takes place in the following manner: The waist belt is applied around the user's waist where after the rear end of the diaper is affixed to the forward portion of the waist belt. The belt is then rotated around the user's waist until the diaper has moved halfway around and is left suspended behind the user's back.

The forward free end of the diaper is finally brought up from between the user's legs and is attached to the waist belt across the user's belly. Since all twisting or bending movements of the body can be avoided throughout the procedure even persons with disabled backs and legs would be able to put on and change diapers without help.

The diaper and waist belts described in the foregoing can be considered as merely exemplifying some embodiments of the inventive concept. A plurality of modifications are conceivable within the scope of the patent claims.

What is claimed is:

1. In combination, an absorbent article having a transverse forward end, a transverse rear end, a longitudinal first side extremity, a longitudinal second side extremity, two forward corners and two rear corners joining the forward end and the rear end, respectively, to the first and second side extremities, and a waist belt for supporting said absorbent article, said waist belt and said absorbent article having coacting hook and loop fabric tape elements thereon by which said absorbent article and said waist belt are releasably secured to each other, said hook fabric tape elements being provided on one of said waist belt and said absorbent article, and said loop fabric tape elements being provided on the other of said waist belt and said absorbent article, wherein said belt comprises a continuous piece of elastic material completely open at top and bottom and having substantially equal width along its entire length, a plurality of said tape elements being arranged in a row spaced from each other along said waist belt and extending over substantially the whole width of said belt, the tape elements provided on said absorbent article comprising two spaced apart forward corner tape elements and two spaced apart rear corner tape elements arranged at said forward and rear corners, respectively, each tape element extending from the adjacent one of said side extremities in the direction of the other side extremity, and said forward and rear corner tape elements being extended outside the side extremities, in the transverse direction.

2. A combination according to claim 1, wherein said waist belt comprises reopenable fastening elements.

3. A combination according to claim 2, wherein said piece of material has two ends, and said reopenable fastening elements comprise coacting hook and loop fabric tape elements, a first one of said tape elements of said reopenable fastening elements being attached to the inside of said piece at one of said ends, and a second one of said tape elements of said reopenable fastening elements being attached to the outside of said piece at the other end thereof.

4. A combination according to claim 1, wherein the plurality of tape elements is arranged along an inner circumference of the waist belt.

5. A combination according to claim 1, wherein the plurality of tape elements is arranged along an outer circumference of said waist belt.

6. In combination, an absorbent article having a transverse forward end, a transverse rear end, a longitudinal first side extremity, a longitudinal second side extremity, two forward corners and two rear corners joining the forward end and the rear end, respectively, to the first and second side extremities, and a waist belt for supporting said absorbent article, said waist belt and said absorbent article having coacting hook and loop fabric tape elements thereon by which said absorbent article and said waist belt are releasably secured to each other, said hook fabric tape elements being provided on one of said waist belt and said absorbent article, and said loop fabric tape elements being provided on the other of said waist belt and said absorbent article, wherein said belt comprises a continuous piece of elastic material completely open at top and bottom and having substantially equal width along its entire length, a plurality of said tape elements being arranged in a row spaced from each other along said waist belt and extending over substantially the whole width of said belt, the tape elements provided on said absorbent article comprising two spaced apart forward corner tape elements and two spaced apart rear corner tape elements arranged at said forward and rear corners, respectively, each tape element extending from the adjacent one of said side extremities in the direction of the other side extremity, and said absorbent article further comprising a forward end flap with one of the tape elements provided on said absorbent article extending in the longitudinal direction outside the transverse forward end of the article.

7. A combination according to claim 6, wherein said waist belt comprises reopenable fastening elements.

8. A combination according to claim 7, wherein said piece of material has two ends, and said reopenable fastening elements comprise coacting hook and loop fabric tape elements, a first one of said tape elements of said reopenable fastening elements being attached to the inside of said piece at one of said ends, and a second one of said tape elements of said reopenable fastening elements being attached to the outside of said piece at the other end thereof.

9. A combination according to claim 6, wherein the plurality of tape elements is arranged along an inner circumference of the waist belt.

10. A combination according to claim 6, wherein the plurality of tape elements is arranged along an outer circumference of said waist belt.

11. In combination, an absorbent article having a transverse forward end, a transverse rear end, a longitudinal first side extremity, a longitudinal second side extremity, two forward corners and two rear corners joining the forward end and the rear end, respectively, to the first and second side extremities, and a waist belt for supporting said absorbent article, said waist belt and said absorbent article having coacting hook and loop fabric tape elements thereon by which said absorbent article and said waist belt are releasably secured to each other, said hook fabric tape elements being provided on one of said waist belt and said absorbent article, and said loop fabric tape elements being provided on the other of said waist belt and said absorbent article, wherein said belt comprises a continuous piece of elastic material completely open at top and bottom and having substantially equal width along its entire length, a plurality of said tape elements being arranged in a row spaced from each other along said waist belt and extending over substantially the whole width of said belt, the tape elements provided on said absorbent article comprising two spaced apart forward corner tape elements and two spaced apart rear corner tape elements arranged at said forward and rear corners, respectively, each tape element extending from the adjacent one of said side extremities in the direction of the other side extremity, and said absorbent article further comprising a rear end flap with one of the tape elements provided on said absorbent article extending in the longitudinal direction outside the transverse rear end of the article.

12. A combination according to claim 11, wherein said waist belt comprises reopenable fastening elements.

13. A combination according to claim 12, wherein said piece of material has two ends, and said reopenable fastening elements comprise coacting hook and loop fabric tape elements, a first one of said tape elements of said reopenable fastening elements being attached to the inside of said piece at one of said ends, and a second one of said tape elements of said reopenable fastening elements being attached to the outside of said piece at the other end thereof.

14. A combination according to claim 11, wherein the plurality of tape elements is arranged along an inner circumference of the waist belt.

15. A combination according to claim 11, wherein the plurality of tape elements is arranged along an outer circumference of said waist belt.

16. In combination, an absorbent article having a transverse forward end, a transverse rear end, a longitudinal first side extremity, a longitudinal second side extremity, two forward corners and two rear corners joining the forward end and the rear end, respectively, to the first and second side extremities, and a waist belt for supporting said absorbent article, said waist belt and said absorbent article having coacting hook and loop fabric tape elements thereon by which said absorbent article and said waist belt are releasably secured to each other, said hook fabric tape elements being provided on one of said waist belt and said absorbent article, and said loop fabric tape elements being provided on the other of said waist belt and said absorbent article, wherein said belt comprises a continuous piece of elastic material completely open at top and bottom and having substantially equal width along its entire length, a plurality of said tape elements being arranged in a row spaced from each other along said waist belt and extending over substantially the whole width of said belt, and wherein said absorbent article, at each corner, further comprises a transverse end flap carrying one of said tape elements provided on said absorbent article and extending in the transverse direction outside the adjacent side extremity.

17. A combination according to claim 16, wherein the tape elements provided on said absorbent article further include at least one forward and at least one rear tape element arranged at the forward and rear ends, respectively, in spaced apart relationship between said forward and rear flap tape elements.

18. A combination according to claim 16, wherein said waist belt comprises reopenable fastening elements.

19. A combination according to claim 18, wherein said piece of material has two ends, and said reopenable fastening elements comprise coacting hook and loop fabric tape elements, a first one of said tape elements of said reopenable fastening elements being attached to the inside of said piece at one of said ends, and a second one of said tape elements of said reopenable fastening elements being attached to the outside of said piece at the other end thereof.

* * * * *